United States Patent [19]

Pettijohn

[11] 4,116,238

[45] Sep. 26, 1978

[54] HIGH VOLTAGE CONSTANT CURRENT SOURCE FOR IONTOPHORESIS

[75] Inventor: David Pettijohn, Watertown, Mass.

[73] Assignee: Midgard Electronics Company, Inc., Watertown, Mass.

[21] Appl. No.: 715,538

[22] Filed: Aug. 18, 1976

[51] Int. Cl.² ............................................. A61N 1/30
[52] U.S. Cl. .................................. 128/172.1; 363/21
[58] Field of Search ............... 128/2 E, 2.1 P, 2.1 E, 128/303.14, 172.1; 321/2, 16; 331/112; 323/4; 363/20, 21

[56] References Cited

U.S. PATENT DOCUMENTS

| | | | |
|---|---|---|---|
| 3,304,517 | 2/1967 | Yamanaka et al. | 321/2 X |
| 3,311,805 | 3/1967 | Kittl et al. | 321/2 |
| 3,421,069 | 1/1969 | Minks | 321/2 |
| 3,541,420 | 11/1970 | Rees | 321/2 X |
| 3,541,420 | 11/1970 | Rees | 363/21 X |
| 3,812,858 | 5/1974 | Oringer | 128/303.14 |
| 3,923,063 | 12/1975 | Andrews et al. | 128/303.14 |
| 3,958,168 | 5/1976 | Grundberg | 321/2 |

Primary Examiner—A. D. Pellinen
Attorney, Agent, or Firm—Weingarten, Maxham & Schurgin

[57] ABSTRACT

A regulated current high voltage source for use in driving an iontophoresis probe. The source provides a highly regulated current to the iontophoresis probe up through voltages substantially in excess of a kilovolt in order to maintain the probe ion injection rate under conditions of partial probe blockage. The source employs a DC-to-DC inverter, comprising a blocking oscillator and pulse transformer, with the load provided in the output circuit of the transformer in a feedback arrangement to a regulating amplifier and driver circuit for the DC input to the pulse transformer and blocking oscillator. A separate timing oscillator having a period of several seconds is optionally employed to disable the source and eliminate the high voltage output in order to generate intermittent ion injection.

2 Claims, 2 Drawing Figures

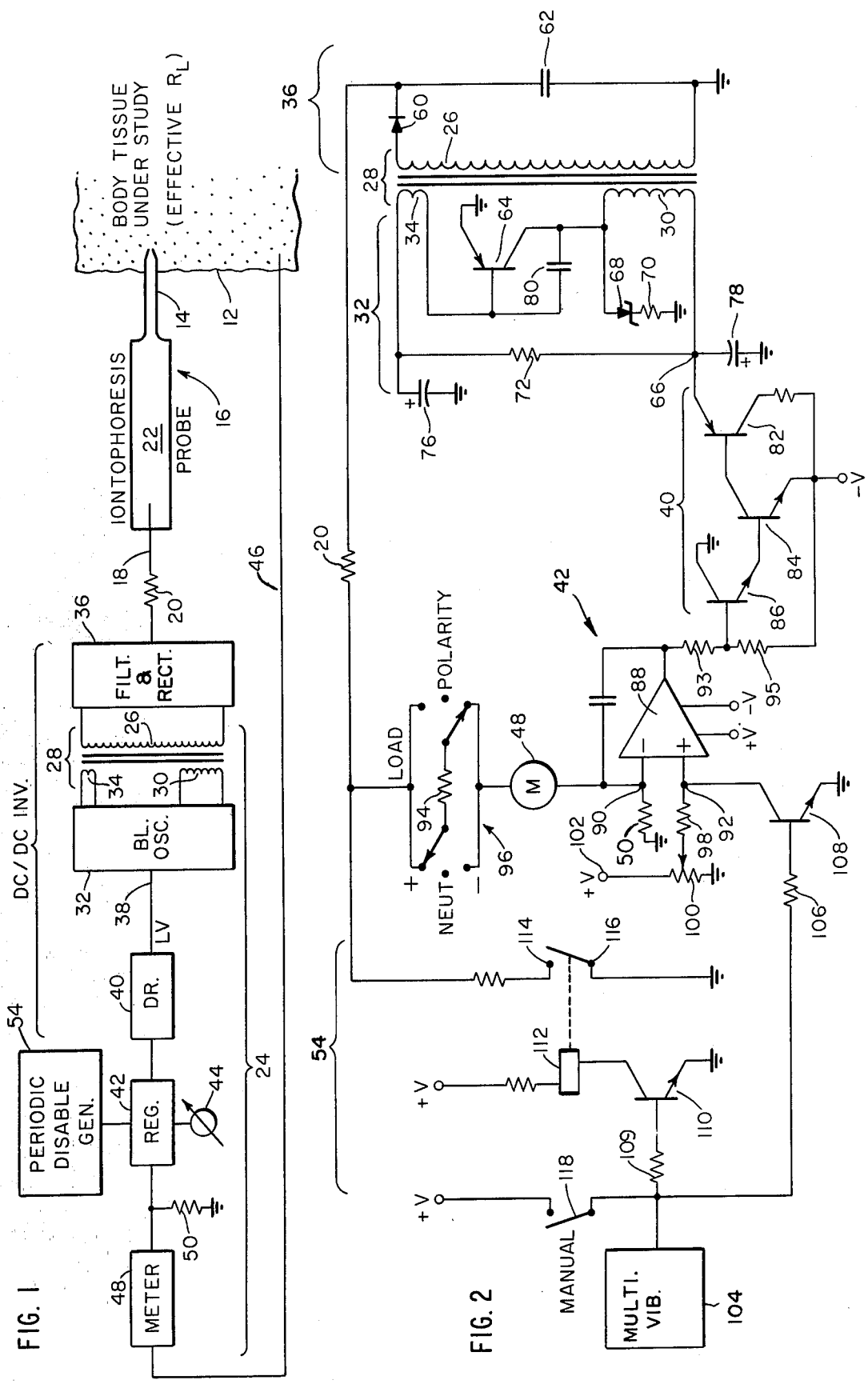

HIGH VOLTAGE CONSTANT CURRENT SOURCE FOR IONTOPHORESIS

FIELD OF THE INVENTION

The present invention relates to regulated current sources and in particular to a current source for use in driving an iontophoresis probe.

BACKGROUND OF THE INVENTION

In anatomical studies aimed at tracing the path of body sensory signals between the location of a stimulus and the brain cortex, it is common to use an iontophoresis probe to inject a controlled and constant rate of ions into the region of the body under study with a resulting effect upon the cortex area responsive to that region of stimulation permitting the correlation of source and receptor sights. The iontophoresis probe typically comprises a pipette having a very narrow opening, as small as 5 microns, through which ions generated within the probe are applied to the anatomical specimen. The ions are generated by electrolytic reaction within the pipette from voltage applied to it from an external source. Typical electrolytes include HRP (HORSERADISH, PEROXIDASE) or TPL (TRITIATED PROLINE OR LEUCINE).

In effect, the electrolyte converts the electrical voltage applied to the pipette into an ionic current which then flows into the body when the body is made a part of the circuit with the current source. It is important to maintain a constant flow of ions at a relatively low current level, typically measured in small numbers of microamperes, for valid and accurate use of the iontophoresis technique. While it is possible to maintain well regulated currents of this level under normal conditions, the pipettes used in iontophoresis, particularly those with small apertures, are subject to clogging through blood clots, air bubbles, or other mechanisms. Such clogging drastically increases the impedance of the pipette circuit through the electrolyte and body under study from megohm ranges up to near open circuit conditions. Such blockages can impede or eliminate the flow of ions from the pipette to the body resulting in abandonment of the experiment

BRIEF SUMMARY OF THE INVENTION

It has been discovered that the effect of clogging of pipettes and other phenomenon contributing to a drastic increase in the impedance of the pipette and body circuit can be counteracted using a current source which has the capability to provide instantaneously, upon demand, extremely high voltage outputs to counteract the drastic increase in impedance and in effect to flush out the pipette clog. Such high voltages, up to substantially over a kilovolt, required to clear a clogged pipette under operating conditions without interruption of the iontophoresis effect, is achieved in a current source according to the present invention in which a DC-to-DC inverter featuring a pulse transformer and blocking oscillator is provided to generate a high voltage output in response to a relatively low voltage input. The high voltage output is applied to the iontophoresis probe and body circuit in a closed loop. The current flowing in this loop is sensed at a low voltage level and regulated at low voltage with the regulated low voltage signal used to drive the blocking oscillator in the primary of the pulse transformer.

The combination of low voltage regulation permits very accurate output current regulation within less than a percent and in combination with the DC-to-DC inverter permits the realization of extremely high output voltages, typically 1,500 volts, where necessary to overcome the effect of pipette clogging as normally encountered in the iontophoresis process.

An optional oscillator having a long period of several seconds is employed to intermittently disable the output of the DC-to-DC inverter so as to provide intermittent operation of the iontophoresis probe. This intermittent operation is advantageous in circumstances where continuous operation might damage the tissue under study.

The low voltage control and regulation circuitry is provided with an adjustment in the low voltage output used to drive the DC-to-DC inverter so that the current applied to the iontophoresis probe may be regulated at any desired level.

DESCRIPTION OF THE DRAWING

These and other features of the present invention are more fully set forth below in the detailed description presented purely for purposes of illustration and not by way of limitation and in the accompanying drawing of which:

FIG. 1 is a generalized block diagram of the current source according to the present invention illustrating its use in iontophoresis techniques; and FIG. 2 is a detailed schematic diagram of the current source circuitry of the present invention.

DETAILED DESCRIPTION OF THE INVENTION

The present invention contemplates a current source particularly adapted for use in driving an iontophoresis probe in a manner to provide a high voltage output to the probe under conditions of probe clogging or other phenomenon resulting in a very high increase in probe circuit impedance that would otherwise terminate the flow of a regulated source of ions to the body site under study.

With reference not to FIG. 1, there is shown a generalized block diagram illustrative of the present invention in its application as a regulated current source for an iontophoresis pipette probe. As shown in FIG. 1 the tissue 12 of a body under study has the tip 14 of an iontophoreses pipette probe 16 applied therein to a region to be stimulated by the regulated and constant flow of a desired ion such as from electrolysis of HRP or TPL. The application of such ions is utilized for such purposes as correlating stimulus source and receptor regions.

The probe 16 is energized by current through a lead 18 which may include a current limiting resistor 20 of very high, several megohm resistance, to prevent excessive current drain in the case of short circuit conditions. The probe 16 is typically of pipette construction having within the central region 22 an electrolyte of one of the above-identified or other materials suitable for use in iontophoresis. The electrolyte is contacted by an extension of the lead 18 into the pipette probe 16.

Current for electrolytic reaction within the probe 16 is supplied by a current source 24 in accordance with the present invention to provide regulated current of a selected magnitude in combination with the ability to achieve high voltage application through the probe 16 to correct or compensate for extraordinary high and varying impedances encountered as, for example, from clogging of the tip 14. Such an effect is achieved by driving current through the lead 18 from a high voltage secondary 26 of a pulse transformer 28 with a voltage capability of typically 1,500 volts to overcome the high impedances in contrast to normal operating voltages of a few hundred volts or less. Transformer 28 is driven at its primary coil 30 by a transistor blocking oscillator 32 having a feedback coil 34 to promote and control oscillation. The pulse transformer 28 typically provides a step-up of 3 : 1000 in voltage and generates a squarewave output at the secondary 26 which is rectified and filtered in a filter-rectifier module 36.

Low voltage of a regulated and preselected magnitude is, on the other hand, applied to the blocking oscillator 32 at a level which is more readily dealt with using highly accurate transistor and integrated circuit control circuitry. The low voltage signal applied to the blocking oscillator 32 on a lead 38 is buffered by a driving circuit 40 to provide sufficient current for driving the blocking oscillator 32 and pulse transformer 28. The driver 40 receives a regulated DC signal from a regulator 42 having a control 44 to adjust the magnitude to which the voltage applied to the driver, and ultimately, transformer 28 is regulated.

To provide current regulation, negative feedback is received from the body tissue 12 through a connection 46 in series with a meter 48, useful in adjusting the control 44, to the regulator 42. The current flowing through the lead 46, the same current which is applied through the probe 16 to the tissue 12, is converted to voltage through a resistor 50 for application to the regulator 42. The regulator 42 operates to maintain a set relationship between the voltage signal applied to regulator 42 by action of resistor 50 and a reference signal supplied by the setting of the control 44. Elements 40, 32, 28 and 36 are viewed as a DC-to-DC inverter in the example of the detailed description. In this manner, the control circuitry and in particular the regulator 42, driver 40, and blocking oscillator 32 are all operated at low voltage permitting accurate regulation using transistor circuitry. High voltage is generated through the pulse transformer 28 and filter circuit 36 permitting and making available high voltage signals upon demand to respond to abnormal, high impedance conditions of the probe 16.

As an optional feature of the current source of the present invention, a periodic disable generator 54 is provided to disable the regulator 42 and shunt its control function so as to remove the output voltage applied through the driver 40 to the blocking oscillator 32 thereby removing the output voltage from the secondary winding 26 and interrupting the flow of current to the probe 16. The generator 54 is typically operated at a period of several seconds per cycle in an automatic mode to interrupt the operation of the probe 16 and the supply of ions through the tip 14 in order to permit the tissue 12 to recover periodically and prevent its saturation and injury in the operation.

With reference now to FIG. 2, the complete circuitry in accordance with the preferred embodiment for the present invention is shown. It is to be understood that deviations from the specifically indicated circuitry are contemplated within the scope of the invention. In particular, the transformer 28 is shown in FIG. 2 to have secondary winding 26 in series with a rectification diode 60 and filter capacitor 62 with an output taken across the capacitor 62 between circuit common and the junction with the diode 60. The primary coil 30 is connected on one end to the collector of a common emitter transistor 64 used as a blocking oscillator. The other end of primary coil 30 receives on a terminal 66 the regulating low voltage DC for the blocking oscillator. A zener diode 68 in series with a resistor 70 connects the collector of transistor 64 to ground as a protection against excessive voltages at the output of the transformer 28 under conditions of open circuit load. The feedback coil 34 in the primary of pulse transformer 28 is connected between the base of the transistor 64 and the terminal 66 through a current limiting resistor 72. Stabilization capacitors 76, 78 and 80 are provided respectively to ground from coil 34 and terminal 66 and between the base and collector of transistor 64.

The driver circuit 40 includes a series of buffer transistors 82, 84 and 86 with the transistors 82 and 86 emitter-follower coupled and the collector transistor 84 coupled into the base of the transistor 82. The three transistors 82, 84 and 86 buffer the output of an amplifier 88 having differential inputs 90 and 92. The output of the amplifier 88 is applied through a voltage divider composed of resistors 93 and 95 to the base of transistor 86.

The amplifier 88 is preferably a high gain FET input transistorized or monolithic amplifier with a response time of at least a few microseconds. The inverting input 90 receives feedback current from the output of the secondary 26 as applied through a limiting resistor 20 and the load 94 of pipette and body tissue through a double pole, double throw, center off-switch 96, which provides polarity reversal. Current meter 48 is also provided in the feedback circuit.

The noninverting input 92 of amplifier 88 is supplied with a variable reference voltage through a resistor 98 from a potentiometer 100 adjusted in potential between a positive voltage 102 and ground.

The periodic disable generator 54 includes a multivibrator 104 operating in an astable mode to provide a periodic squarewave or rectangular wave output through a resistor 106 to the base of transistor 108 operative to periodically ground the noninverting input 92 forcing the output of the amplifier 88 to assume a value which eliminates the drive voltage applied to the blocking oscillator transistor 64. The same output from the multivibrator 104 is also applied through an input resistor 109 to the base of a transistor 110. Transistor 110 drives a relay 112 in its collector circuit. The relay 112 when energized closes a set of contacts 114 and 116 to connect the load 94 to ground during the period of nonenergization to prevent continued energization from the stored charge in the capacitor 62. A Switch 118 is provided to permit deactivation of the periodic disable generator 54 as by maintaining an on bias at its output as may be desired or not by the particular conditions of operation.

The above-described specific implementation for the preferred embodiment of the present invention is to be considered as exemplary only with alterations and improvements intended to fall within the scope of the invention as limited only in accordance with the following claims.

What is claimed is:

1. A high voltage DC regulated blockage clearing current source and iontophoresis system comprising:
   an animal body under study;
   an iontophoresis probe located for ion injection into said body;

a DC-to-DC inverter providing a relatively high voltage rectified DC squarewave output in response to a relatively low voltage DC input;

a feedback circuit responsive to the rectified DC squarewave voltage output at said relatively high voltage and including in circuit said iontophoresis probe and animal body under study in which the inverter output is applied to said probe;

means responsive to the magnitude of current flowing through said feedback circuit for developing a DC signal representative of the magnitude thereof; and means for applying said DC signal as the relatively low voltage DC input to said DC-to-DC inverter in a polarity to provide negative feedback in said feedback circuit and to maintain a predetermined current from said inverter to said probe; and means for adjusting the level of said DC signal applied to said DC-to-DC inverter to adjust the regulated magnitude of the relatively high voltage DC output of said DC-to-DC inverter to operate in the range of a few hundred volts or less in the absence of probe blockage and a relatively high current in said feedback circuit and to operate in a range of at least approximately 1500 volts in response to a probe blockage and a relatively low current in said feedback circuit.

2. The source of claim 1 further including an indicator of the current flowing through said iontophoresis probe.

* * * * *